United States Patent [19]

Ziegenhagen et al.

[11] 4,029,714

[45] June 14, 1977

[54] ETHYLENE/CHLORINE ELIMINATION PROCESS

[75] Inventors: Allyn J. Ziegenhagen; Ramsey G. Campbell, both of Berkeley, Calif.

[73] Assignee: Stauffer Chemical Company, Westport, Conn.

[22] Filed: Nov. 5, 1975

[21] Appl. No.: 629,171

[52] U.S. Cl. .................. 260/658 R; 260/662 R
[51] Int. Cl.² .......................................... C07C 17/00
[58] Field of Search .................. 260/662 R, 658 R

[56] References Cited

UNITED STATES PATENTS

| | | | |
|---|---|---|---|
| 2,160,574 | 5/1939 | Hennig | 260/662 R |
| 2,246,082 | 6/1941 | Vaughan et al. | 260/662 R |
| 2,393,367 | 1/1946 | Hammond | 260/662 R |
| 3,652,693 | 3/1972 | Mulders et al. | 260/662 R |

Primary Examiner—Delbert E. Gantz
Assistant Examiner—Joseph A. Boska
Attorney, Agent, or Firm—M. Henry Heines; Michael J. Bradley

[57] ABSTRACT

An improvement in a process for recovering residual amounts of ethylene in ethylene chlorination effluents is disclosed, whereby ureacted chlorine is virtually eliminated. Elimination of the chlorine is accomplished by reacting it with the clorinated hydrocarbons in the stream over a novel ferric chloride catalyst mixture.

9 Claims, 2 Drawing Figures

ETHYLENE/CHLORINE ELIMINATION PROCESS

BACKGROUND OF THE INVENTION

In many processes for the chlorination or oxychlorination of ethylene, the conversion of ethylene is substantially less than complete. Thus, the effluent from a conventional oxychlorination reactor will contain, in addition to reaction products, from 0.1 percent to 15 percent or even 20 percent by weight unreacted ethylene, as well as HC1, $O_2$, inert gases, etc. In view of the current environmental concern for maintaining hydrocarbon levels in the atmosphere as low as possible, as well as the high cost of ethylene, the recovery of the unreacted ethylene is a practical necessity.

Previous work in this area has evolved ethylene recovery systems which provided recovery of the majority of residual ethylene. French Pat. No. 1,421,903 and Belgian Pat. No. 718,777 disclose exemplary prior art procedures. However, as indicated, environmental and cost requirements now demand that virtually one hundred percent conversion of the feed ethylene be achieved.

Many current oxychlorination processes have attempted to solve this problem by the use of an ethylene clean-up reactor situated at the exit of the oxychlorination system. In one example of such a reactor, the ethylene in an oxychlorination effluent is reacted with chlorine to produce 1,2-dichloroethane (hereinafter referred to as ethylene dichloride or EDC), in the presence of an activated alumina catalyst. The EDC produced in the clean-up reactor can then be combined with that produced in the oxychlorination system. As the clean-up reactor, commercial plants commonly use a multi-tube reactor with a fixed bed catalyst. Inlet temperatures range from about 50° C to about 200° C, and the temperature of the gas in the catalyst bed ranges from about 100° C to about 300° C. The pressure ranges from about 15 psig to about 75 psig, the space velocity (which is defined as volume of gas at 0° C and atmospheric pressure per hour per volume of catalyst bed) ranges from about 500 to about 5000 hour$^{-1}$, and the contact time ranges from about 0.7 to about 32 sec. The chlorine is fed at about 5% molar deficit to about 10% molar excess with respect to the ethylene.

Small amounts of both chlorine and ethylene pass through the reactor unreacted and are present in the effluent. The amounts of each vary considerably with the chlorine-to-ethylene feed ratio. It is possible to maintain low levels of each by maintaining a constant feed ratio with a slight chlorine excess controlled to within one tenth of a percent. Such control would require continuous and accurate monitoring of the ethylene content in the ethylene-containing stream and highly accurate control of the chlorine feed rate. Such accuracy is difficult to achieve in commercial plant scale equipment, especially when fluctuations in operating conditions are encountered. Furthermore, the kinetics of the reactions place a lower limit on the amounts of each component which remain unreacted.

Emissions containing ethylene on the order of several thousand ppm and chlorine on the order of several hundred ppm are common in existing plants which use the ethylene clean-up system described above. The large excess of ethylene in these emissions may arise from a desire to avoid the consequences of chlorine in the atmosphere, examples of which are unpleasant odor and toxicity to plant life. A system was needed, therefore, which would convert a larger portion of the ethylene to EDC while avoiding the odor problem caused by chlorine. This goal is accomplished by placing a chlorine-removal system immediately downstream of the ethylene clean-up system described hereinabove and operating the combination at a greater chlorine-to-ethylene feed ratio. Chlorine removal is effectively achieved by catalyzing a reaction between chlorine and the hydrocarbons in the stream by addition or substitution reactions. In this manner, small amounts of hydrocarbons are chlorinated and partially chlorinated hydrocarbons are further chlorinated.

A variety of catalysts are known in the art to be active for this purpose, for example, alkaline earth chlorides, cupric chloride, and ferric chloride. Ferric chloride is known to catalyze oxychlorination or direct chlorination mechanisms, in both gas and liquid phase systems. Inert catalyst supports are frequently used in gas phase reactions to provide porosity and high surface area on which the reaction can take place. A recurring problem with a supported ferric chloride catalyst is the decline in activity over extended use of the catalyst. Although a precise reason for the decline is unknown, changes in the valence of the iron, the formation of iron oxides and volatilization of ferric chloride are possible contributors.

The objects of the present invention are to provide a chlorine removal system in which a high level of activity is maintained over an extended period of time, and to eliminate ethylene from an ethylene-containing stream by contacting the stream with chlorine in such a manner that both ethylene and chlorine are substantially eliminated from the vent gas.

SUMMARY OF THE INVENTION

In brief, the invention comprises a novel ethylene clean-up process in which a novel catalyst mixture is used which comprises a mixture of metallic iron and particles of activated alumina which are impregnated with ferric chloride either by prior treatment or by in situ metallic iron. The ethylene is reacted with an excess of chlorine in a first reaction zone or series of zones over a catalyst bed comprising activated alumina to produce EDC. The effluent, which comprises EDC, other saturated chlorinated hydrocarbons, some ethylene, and unreacted chlorine, is then reacted over the aforesaid ferric chloride catalyst in a second reaction zone in which a portion of the EDC and other saturated chlorinated hydrocarbons present is further chlorinated, reducing the concentration of the unreacted chlorine to less than about 200 ppm by volume.

In another aspect, the invention comprises a process for eliminating chlorine from a waste stream rich in chlorine and partially chlorinated saturated hydrocarbons which comprises reacting said waste stream over the aforesaid ferric chloride catalyst.

Substantial benefit is achieved by the use of the process of the invention in either of the aspects enumerated above. For example, the process is capable of handling a wide range of chlorine excess with respect to ethylene in the feed to an ethylene clean-up reactor, when the process of the invention is used in conjunction with an ethylene clean-up reactor. Similarly, the process is capable of handling a wide range of chlorine concentration when the process of the invention is used to remove chlorine from a waste stream rich in chlorine and partially chlorinated saturated hydrocarbons. Furthermore, although similar results might be attained in a very long catalyst bed consisting of bare activated alumina, the process of the invention achieves the desired results in a catalyst bed of relatively short length. This is of particular advantage to the application of the invention to existing plants, and in the economical design of new plants. Finally, the process of the invention has the advantage of maintaining a high level of activity in chlorine removal over a period of time by the in situ generation and deposition of catalytic ferric chloride on the activated alumina support.

Although the primary reactions occurring in the chlorine removal system described above are substitution reactions, the process of the invention is also useful in prolonging the activity of ferric chloride in catalyzing addition reactions. In fact, any chlorination reaction catalyzed by ferric chloride and subject to catalyst deactivation will benefit from the process of the invention. Examples of such reactions are addition reactions of chlorine or HCl across double or triple bonds and the oxychlorination of olefins.

Although the process of the invention can be conveniently used as an ethylene clean-up process in connection with an ethylene oxychlorination process, the process of the invention is equally well-suited to the treatment of any ethylene-containing stream in which it is desired to recover the ethylene as EDC, when used in conjunction with the clean-up reactor described above in the background of the invention. Furthermore, in addition to its use for the treatment of the effluent from an ethylene clean-up system of the type described in the background of the invention, the process of the invention can be used to reduce the chlorine content of any waste stream rich in chlorine and saturated hydrocarbons or chlorohydrocarbons, regardless of the source of the stream.

Although varying pollution control restrictions are in effect throughout the world, a working goal for the process of the present invention is to achieve an ethylene content less than about 50 ppm (vol) and a chlorine content less than about 200 ppm (vol). The process of the invention can also be used to achieve levels of ethylene as low as 1 ppm and chlorine as low as 5 ppm by adjustment of reaction temperatures and residence times, and is therefore not limited in performance to the levels stated above.

Examples of embodiments of the process of the invention are illustrated in the attached drawings, in which:

FIG. I represents a generalized flow sheet depicting the invention as it is used for the removal of chlorine from a waste stream rich in chlorine and partially chlorinated, saturated hydrocarbons.

FIG. II represents a flow sheet depicting the invention in combination with an ethylene clean-up system.

DETAILED DESCRIPTION OF THE INVENTION

Figure 1:
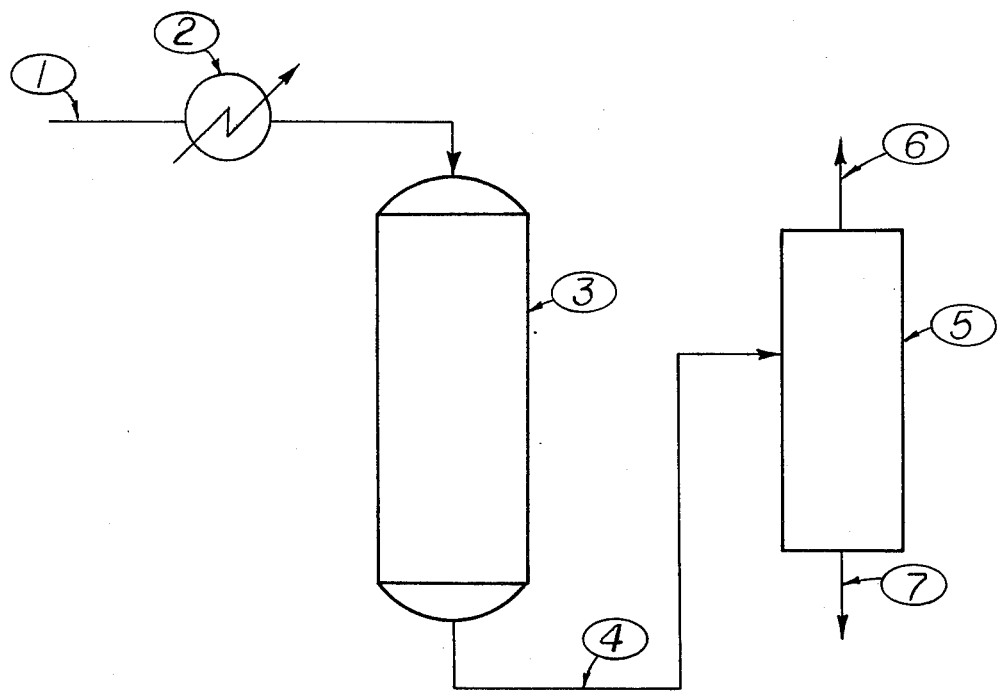
Figure 2:
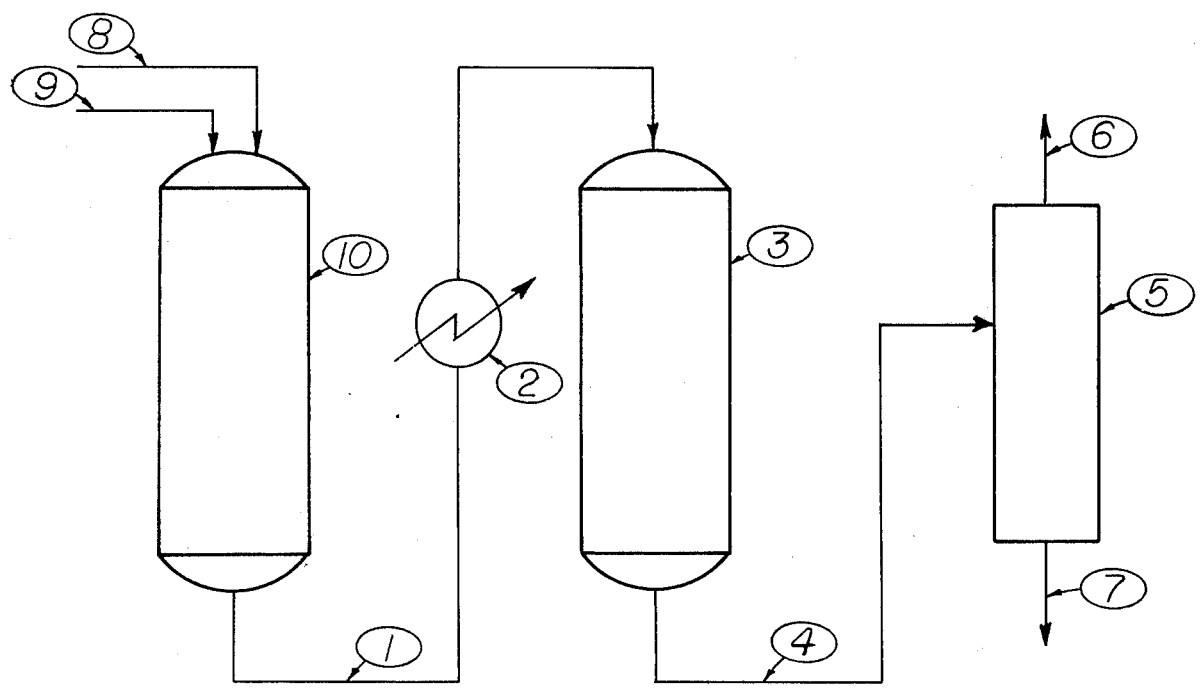

FIG. I is a generalized drawing of the process of the present invention, in which the invention is depicted as a process for eliminating chlorine from a waste stream rich in chlorine and hydrocarbons and/or partially chlorinated hydrocarbons, the chlorine comprising up to 20% by volume of the mixture. This stream may be taken from the effluent of an ethylene clean-up process in which an excess of chlorine is used to react with the unreacted ethylene contained in the effluent of any ethylene-consuming process, or more particularly of an ethylene chlorination or oxychlorination process. The steam may contain undesired by-produced in the ethylene-consuming process, most of which are saturated and either partially chlorinated or not chlorinated at all. Alternatively, the stream may be derived from any source and may consist of any saturated and either partially chlorinated or unchlorinated hydrocarbons and chlorine, of which removal of the chlorine is desired. Line 1 carries this chlorine-rich stream to heat exchanger 2 which raises the temperature of the stream to between about 90°C and about 250°C, preferably to between about 100°C and about 180°C. The contents of line 1 are then passed into reactor 3 which is a fixed bed catalytic reactor comprising a mixture of metallic iron and particles of activated alumina which are impregnated with ferric chloride either by prior treatment or by in situ deposition arising from the action of molecular chlorine on the metallic iron, in which the ratio of the superficial surface area of the iron to the total BET surface area of the alumina ranges from a value equal to 1.5 times the surface area of the inner reactor wall divided by the total BET surface area of the alumina contained therein, or about $1 \times 10^{-7}$, whichever is greater, to about $2 \times 10^{-6}$, preferably from about $2 \times 10^{-7}$. By "total BET surface area" is meant the BET surface area, expressed in $m^2/g$, as the term is known in the art, multiplied by the total weight of the alumina contained in the catalyst bed, and converted to appropriate units such as to render the ratio referred to above dimensionless.

To illustrate the relationship between the surface area of the metallic iron and that of the alumina particles, activated alumina of BET surface area of 240 $m^2/g$ is a typical example. Using this figure, the surface area ratio of the metal to the alumina can be converted to units of square inches of metal surface per pound of alumina. The range of surface area ratio then becomes about 20 to about 375 $in^2$ metal/lb alumina with about 37 to about 84 $in^2$ metal/lb alumina preferred. In the embodiment of the invention in which the alumina is impregnated with ferric chloride by prior treatment, the ferric chloride expressed in terms of weight percent iron comprises from about 0.5% to about 10% of the catalyst particle, with about 2% to about 6% preferred.

The novel catalyst mixture is particularly effective in vessels which do not corrode, thereby preventing reactor failure due to corrosion of the reactor walls.

The term "mixture" is intended to include both a zoned arrangement where layers of metallic iron are alternated with layers of impregnated and/or unimpregnated catalyst and a quasi-homogeneous arrangement where one component of the mixture is randomly or approximately evenly dispersed among the other component. The metallic iron can be in the form of commercially available iron tower packing, scrap iron, or any other form in which iron is present in predominantly metallic form.

Reactor 3 can be either a tank type or a tubular reactor, and it can be designed for either up-flow or down-flow of the reactant gases. Reactor 3 is operated at a temperature of about 90° C to about 250° C, preferably about 100° C to about 180° C. The pressure ranges from about 15 psig to about 75 psig, preferably from about 25 psig to about 60 psig. The space velocity ranges from about 50 to about 1000 $hour^{-1}$, preferably from about 100 to about 500 $hour^{-1}$, and the residence time ranges from about 2 to about 50 seconds, preferably from about 5 to about 30 seconds. The effluent from reactor 3 comprises chlorinated hydrocarbons which are more highly chlorinated in general than those contained in line 1, very small amounts of unreacted ethylene and chlorine, unreacted components from the preceding process, and any gaseous inerts passing through the system. This effluent is passed through line 4 to separation zone 5 wherein the ethylene dichloride and heavier chlorinated impurities are separated and sent to purification through line 7. The balance of the effluent, which is principally inert gases and minor quantities of HC1, is removed through line 6. After removal of HC1 by conventional teahniques, the effluent is of appropriate quality with respect to ethylene and chlorine for venting to the atmosphere. The ethylene level is below 50 ppm and frequently even below 1 ppm by volume, and the chlorine level is below 200 ppm and frequently even below 5 ppm by volume, depending on reaction temperature and residence times.

FIG. II is a drawing of the process of the invention in which the invention is depicted as an improvement in a process for recovering ethylene from an ethylene-containing stream. Line 8 consists of a mixture of ethylene and other components from which it is desired to recover the ethylene by reaction with chlorine to produce EDC. Line 8 may come from the effluent from an ethylene oxychlorination or chlorination system, in which case the mixture will contain chlorinated hydrocarbons, both saturated and unsaturated, and possibly gaseous inerts, for example nitrogen, which have passed through the oxychlorination or chlorination system unreacted. Chlorine is fed through line 9 at about 0.3% molar excess with respect to the ethylene in stream 8. Chlorine and the ethylene-containing mixture are contacted in reactor 10, tubular reactor, in an exothermic reaction over catalyst comprising activated alumina particles either uniform surface area or of a mixture of surface areas either admixed or zoned in layers of approximately constant surface area, preferably with the surface area increasing from the inlet end to the exit end of the reactor. Reactor 10 is designed for either up-flow or down-flow of the reactant gases. The inlet temperature ranges from about 50°C to about 200°C. The maximum reactor temperature ranges from about 100°C to about 300°C. The pressure ranges from about 15 psig to about 75 psig. The space velocity ranges from about 500 hour$^{-1}$ to about 5000 hour$^{-1}$, and the residence time ranges from about 0.7 sec to about 32 sec. The effluent from reactor 10 contains EDC, small quantities of unreacted ethylene, unreacted chlorine, and all other impurities, inerts, and unreacted components which were in either of the feed streams, as well as products produced by side reactions occurring in reactor 10, such as oxidation or reaction of chlorine with compounds other than ethylene. The portion of the drawing extending downstream from the reactor 10 and describing the chlorine-removal portion of the system is identical to FIG. I, and the descriptions above pertaining to FIG. I apply.

As a variation of the flow sheet depicted in FIG. II, reactor 3 can be incorporated into reactor 10 whereby the catalyst bed of reactor 3 becomes an additional zone situated at the downstream end of reactor 10 in the same tubes as the bare activated alumina catalyst of reactor 10. Since the reaction between ethylene and chlorine which occurs in the upstream portion of the multi-zoned reactor of the variation is exothermic, a coolant temperature may be employed which is below the temperature range of reactor 3 in the attached drawings. The reaction occuring in the ferric chloride portion of the reactor, however, is much less exothermic. Consequently, the reaction temperature in the ferric chloride zone will remain close to the coolant temperature. Therefore, in order to achieve the same extent of reaction, the ferric chloride zone would have to be longer if it formed the downstream portion of a multi-zoned tubular reactor than if it were a separate tank-type reactor following a heat exchanger, as depicted in the drawing.

The ferric chloride catalyst is prepared by conventional impregnation techniques utilizing an aqueous solution of ferric chloride and an activated alumina support. The term "activated alumina" as used herein refers to any porous, absorptive form of aluminum oxide which has been produced by the Bayer process or its equivalent from an impure form such as bauxite, and has been heated at a controlled temperature high enough to drive off most of the combined water but low enough to maintain the desired surface area. In the preferred embodiment of the invention, the activated alumina is a spherical particulate alumina having a surface area of at least 100 m$^2$/g, preferably between about 225 and about 275 m$^2$/g, and also an attrition hardness of at least 90%, a total pore volume of between about 0.3 and about 0.8 cc/g, an average pore diameter of about 70 to about 120 A, wherein between about 35 and about 70% of the pore volume is composed of pores having a diameter of between about 80 and about 600 A. Examples of suitable supports of this type are aluminas currently available under the designations HSC-114, from Houdry Process and Chemical Company, and SCM-250, from Rhone-Progil. Other types of activated aluminas will also serve the purpose of the invention, for example, cylindrical pellets or extrudates of varying size, surface areas, pore characteristics, and structural integrity. These variations may require such modifications in system geometry as will be apparent to a person skilled in the art.

In each of the following examples, the experimental data was obtained in an apparatus according to FIG. II. Reactor 10 consisted of one schedule 40 nickel pipe, 12 feet long and 2 inches in diameter, jacketed for its entire length with a 4-inch schedule 40 steel pipe. The heat of reaction was removed by boiling water maintained at a pressure of 15 psig and a temperature of 121°C in the annular space between the two pipes. The hot spot temperature and location inside the catalyst bed was measured by means of a moveable thermocouple inside a quarter inch thermowell which was introduced at the bottom of the reactor and extended throughout length.

The catalyst bed in reactor 10 was divided into three zones, each of length 30 inches. The catalyst used in the upper zone was SA 3235 ¼inch alumina spheres obtained from Norton Chemical Company, and had the following properties:

Bulk Density: 42 ± 4 lb/ft$^3$
Surface Area (BET): 12 ± 4 m$^2$/g
Attrition Hardness: 90%, min.
Loss On Ignition (300°C): 5 wt. %, max..
   Screen analysis (Tyler Screen):

+2.5 mesh: 0.5 wt. %, max.
−2.5, +3.5 mesh: 90 wt. %, min.
−3.5 +4 mesh: 10 wt. %, max.
−4 mesh: 1.0 wt. %, max..

The catalyst occupying the middle zone was SA 3232 1/4 inch alumina spheres, also obtained from Norton Chemical Company and having the following properties:

Bulk Density: 40 ± 3 lb/ft$^3$
Surface Area (BET): 30 ± 5 m$^2$/g
Attrition Hardness: 90 wt. %, min.
Loss on Ignition (300°C): 5 wt. %, max.
 Screen Analysis (Tyler Screen):

+2.5 mesh: 0.5 wt. %, max.
−2.5, +3.5 mesh: 90 wt. %, min.
−3.5, +4 mesh: 10 wt. %, max.
−4 mesh: 1.0 wt. %, max..

The catalyst occupying the bottom zone was HSC-114 1/4 inch alumina spheres obtained from Houdry Division, Air Products and Chemicals, Inc., having the following properties:

Surface Area (BET): 250 ± 25 m$^2$/g
Bulk Density: 40 ± 3 lb/cu.ft.
Loss on Ignition (300° C): 5 wt. %, max.
Attrition Hardness: 90%, min.
Pore Volume, N$_2$: 0.44 cc/g
Average Pore Diameter (BET): 64–70 °A
Pore Volume, 80–600 A Pores : 20–37% to total pore volume.
 Screen Analysis (Tyler Screen):

+3 mesh: 1.0 wt. %, max.
−3, +4 mesh: 27–70 wt. %
−4, +5 mesh: 25 −70 wt. %
−5, +6 mesh: 10 wt. %, max.
−6 mesh: 3 wt. %, max.

Reactor 3 consisted of one schedule 40 steel pipe, 20 feet long and 4 inches in diameter. A nickel liner covered the inner surface of the uppermost 12 feet of the pipe. Steam tracing and insulation around the outside of the pipe formed a thermal barrier which permitted the operation of the reactor as an adiabatic reactor. The catalyst bed in each of the examples below was 90 inches in length and supported in the upper portion of the reactor. The catalyst bed temperature was measured by a movable thermocouple inside a quarter-inch thermowell which was introduced at the top of the reactor and extended throughout its length.

In each example, the feed stream corresponding to line 8 consisted of 7 mole percent ethylene, 1 mole percent oxygen, 4 mole percent EDC, 1 weight percent water, and the balance nitrogen. The inlet pressure to reactor 10 was maintained at 50 psig. The superficial velocity through the reactor, evaluated for an empty reactor at 125°C and 50 psig, was 1.66 feet per second.

In order to calculate the chlorine and HCl concentrations, the exit stream corresponding to line 4 was bubbled through a potassium iodide solution and collected in a water displacement vessel of fixed and known volume. The solution was titrated for HCl with sodium hydroxide, and for chlorine with sodium thiosulfate. In addition, a portion of the exit stream was condensed, and both the liquid and gas phases after condensation were analyzed by gas chromatography. The results were combined with the titrations in an overall material balance from which the percent excess chlorine was calculated as well as the other values shown in the tables.

EXAMPLE I

This example demonstrates the catalyst deactivation which occurs over a period of time when alumina impregnated with ferric chloride is used alone in the reactor 3 catalyst bed. The catalyst used in reactor 3 consisted of HSC 114 alumina, similar to that occupying the bottom zone of the catalyst bed in reactor 10, but impregnated with ferric chloride to yield an iron content of 2 weight percent. The data obtained with this catalyst is shown in Table I.

Column (1) shows the point along the axis of the reactor 3 catalyst bed at which the gas stream was sampled to determine the $C_2H_4$, $Cl_2$, and $HCl_2$, and HCl concentrations shown in Columns (3), (4) and (5). The location of the point is expressed in terms of the residence time of the gases as measured from the top of the reactor 3 catalyst bed down to the sample point, based on an empty tube. Column (2) shows the chlorine content of the feed to reactor 10, expressed in terms of percent excess over the ethylene in the feed. Columns (6) and (7) show respectively the reactor 10 hot spot temperature and the reactor 3 average temperature.

TABLE I

| (1) Reactor 3 Residence Time (Empty Bed) (sec) | (2) % Excess Chlorine | (3) | (4) Reactor 3 Effluent Concentrations (ppm by vl) | (5) | (6) | (7) |
|---|---|---|---|---|---|---|
| | | | | | Temperatures (° C) | |
| | | $C_2H_4$ | $Cl_2$ | HCl | Reactor 10 Hot Spot | Reactor 3 Average |
| Data taken between 0 and 84 hours on stream | | | | | | |
| 17.3 | 6.0 | 17 | 5 | 6,816 | 199 | 166 |
| 17.3 | 6.6 | <1 | 19 | 6,453 | 211 | 167 |
| 17.3 | 6.9 | <1 | 9.7 | 7,999 | 208 | 168 |
| 17.3 | 7.0 | 7.8 | 19 | 7,148 | 209 | 166 |
| 17.3 | 7.0 | 14 | <5 | 7,504 | 197 | 168 |
| 17.3 | 7.4 | 9.1 | 14 | 9,432 | 201 | 164 |
| 17.3 | 8.9 | <1 | 9.8 | 9,995 | 213 | 167 |
| 17.3 | 10.9 | <1 | 5 | 13,142 | 201 | 169 |
| 17.3 | 12.6 | <1 | 9.8 | 13,914 | 200 | 172 |
| Data taken between 84 and 112 hours on stream | | | | | | |
| 17.3 | 3.7 | 521 | 5.1 | 5,091 | 194 | 151 |
| 17.3 | 4.3 | 418 | 5.0 | 5,799 | 193 | 156 |
| 17.3 | 4.4 | 297 | 5.0 | 5,425 | 192 | 152 |
| 17.3 | 5.1 | 172 | 5.0 | 196 | 151 | |
| 17.3 | 6.8 | 7.7 | 5.0 | 9,122 | 193 | 156 |
| 17.3 | 7.5 | <1 | 5.0 | 8,413 | 195 | 158 |
| 17.3 | 7.5 | 1.9 | 5.1 | 9,351 | 194 | 156 |
| 17.3 | 8.4 | <1 | 20 | 10,333 | 204 | 153 |
| Data taken between 182 and 203 hours on stream | | | | | | |
| 17.3 | 3.5 | <1 | 9.4 | 2,531 | 200 | 157 |
| 17.3 | 3.9 | <1 | 6.5 | 2,947 | 200 | 158 |

TABLE I-continued

| (1) Reactor 3 Residence Time (Empty Bed) (sec) | (2) % Excess Chlorine | (3) | (4) Reactor 3 Effluent Concentrations (ppm by vl) | (5) | (6) Temperatures (° C) | (7) |
|---|---|---|---|---|---|---|
| | | $C_2H_4$ | $Cl_2$ | HCl | Reactor 10 Hot Spot | Reactor 3 Average |
| 17.3 | 7.1 | <1 | 449 | 2,915 | 205 | 160 |
| 17.3 | 8.6 | <1 | 1,102 | 3,831 | 205 | 161 |
| 17.3 | 8.9 | <1 | 5 | 6,719 | 202 | 160 |
| 17.3 | 9.0 | <1 | 2,810 | 4,764 | 205 | 160 |
| 17.3 | 9.5 | <1 | 37 | 7,280 | 201 | 159 |
| 17.3 | 13.5 | <1 | 5,368 | 3,883 | 201 | 162 |

Columns (2) and (4) show that during the first 112 hours or operation, the amount of chlorine still unreacted at residence time 17.3 sec remained below 20 ppm at chlorine excesses in the feed of up to 12.6%. Later in the run, however, between 182 and 203 hours on stream, substantially greater amounts of chlorine appeared at the same point in the reactor at chlorine excesses in the feed of as low as 7%. This indicates a substantial loss of catalytic activity over time.

EXAMPLE II

The catalyst bed in this run consisted of ⅝ inch steel Pall rings in layers 2.75 inches thick alternating with 12.25 inch layers of the catalyst used in Example I (HSC 114 alumina impregnated with ferric chloride to yield an iron content of 2 weight percent). The Pall rings thus constituted approximately 18 volume percent of the catalyst bed. Consequently, the amount of catalyst used was 18% less than that used in Example I. The catalyst bed length and all operating conditions were the same as those of Example I. The data obtained between 220 and 252 hours on stream are shown in Table II, to which the description pertaining to Table I above applies.

TABLE II

| (1) Reactor 3 Residence Time (Empty Bed) (sec) | (2) % Excess Chlorine | (3) | (4) Reactor 3 Effluent Concentrations (ppm by vol) | (5) | (6) Temperatures (° C) | (7) |
|---|---|---|---|---|---|---|
| | | $C_2H_4$ | $Cl_2$ | HCl | Reactor 10 Hot Spot | Reactor 3 Average |
| Data taken between 220 and 252 hours on stream | | | | | | |
| 17.3 | 5.4 | <1 | <5 | 4,307 | 199 | 160 |
| 17.3 | 8.5 | <1 | 10 | 9,146 | 200 | 162 |
| 17.3 | 10.0 | <1 | 5 | 10,082 | 207 | 165 |
| 17.3 | 10.1 | <1 | 5 | 10,176 | 199 | 160 |
| 17.3 | 10.5 | 1.6 | 5.3 | 11,354 | 205 | 160 |
| 17.3 | 10.7 | <1 | 5 | 10,034 | 206 | 163 |
| 17.3 | 11.2 | <1 | 407 | 10,461 | 200 | 166 |
| 17.3 | 11.5 | <1 | 1,465 | 10,596 | 206 | 161 |
| 17.3 | 12.0 | <1 | 204 | 12,269 | 200 | 161 |
| 17.3 | 13.0 | <1 | 535 | 11,531 | 198 | 161 |

Columns (3) and (4) indicate that highly efficient chlorine and ethylene removal was observed at chlorine excesses up to about 11%, where a sharp increase in the chlorine content of the reactor 3 effluent occurred. This high level of reactor performance was observed at the beginning of the run and persisted over the entire 252-hour length with no evidence of catalyst deactivation.

What is claimed is:

1. The process for eliminating chlorine and ethylene from a waste stream comprising chlorine at a concentration of up to about 5000 ppm (vol), and unchlorinated and partially chlorinated hydrocarbons, which comprises reacting said waste stream at a temperature between about 90° C and about 250° C and at a pressure between about 15 psig and about 75 psig, at a space velocity between about 50 hour$^{-1}$ and about 2000 hour$^{-1}$ and a residence time between about 2 sec and about 50 sec, over a fixed catalyst bed comprising a mixture of metallic iron and particles of activated alumina impregnated with ferric chloride either by prior treatment or by in situ deposition arising from the action of molecular chlorine on the metallic iron, in which the ratio of the superficial surface area of the iron to the total BET surface area of the alumina ranges from a value equal to 1.5 times the surface area of the inner reactor wall divided by the total BET surface area of the alumina contained therein, of about $1 \times 10^{-7}$, whichever is greater, to about $2 \times 10^{-6}$, to produce an effluent comprising more highly chlorinated hydrocarbons, and less than 200 ppm by volume of chlorine.

2. The process according to claim 1 wherein the particles of activated alumina are impregnated with ferric chloride by prior treatment to between about 0.5% and about 10% by weight (in terms of iron) of the catalyst particle.

3. The process according to claim 1 wherein the particles of activated alumina are impregnated with ferric chloride by prior treatment to between about 2% and about 6% by weight (in terms of iron) of the catalyst particle.

4. The process according to claim 1 wherein the reaction temperature is between about 100°C and about 180°C.

5. The process according to claim 1 wherein the reaction pressure is between about 25 psig and about 60 psig.

6. The process according to claim 1 wherein the space velocity is between about 100 hour$^{-1}$ and about 1000 hour$^{-1}$.

7. The process according to claim 1 wherein the residence time is between about 5 seconds and about 30 seconds.

8. The process according to claim 1 wherein the ratio of the superficial surface area of the iron to the BET surface area of the alumina is between about $2 \times 10^{-7}$ and about $5 \times 10^{-7}$.

9. The process according to claim 1 wherein the particles of activated alumina are impregnated with ferric chloride by prior treatment to between about 2.0% and about 6.0% by weight (in terms of iron) of the catalyst particle, the reaction temperature is between about 100° C and about 180° C, the reaction pressure is between about 25 psig and about 60 psig, the space velocity is between about 100 hour$^{-1}$ and about 1000 hour$^{-1}$, the residence time is between about 5 and about 30 seconds, and the ratio of the superficial surface area of the iron to the BET surface area of the alumina is between about $2 \times 10^{-7}$ and about $5 \times 10^{-7}$.

* * * * *

UNITED STATES PATENT OFFICE
CERTIFICATE OF CORRECTION

Patent No. 4,029,714            Dated June 14, 1977

Inventor(s) Allyn J. Ziegenhagen et al.

It is certified that error appears in the above-identified patent and that said Letters Patent are hereby corrected as shown below:

Column 4, line 24, the number reading "$10^{-7}$" should read -- $10^{-7}$ to about $5 \times 10^{-7}$ --.

Column 5, line 32, the number reading "0.3%" should read -- 0.3% to about 10% --.

Table I, Column 5, the number reading "196" should read -- 6,211 --.

Table I, Column 6, the number reading "151" should read -- 196 --.

Table I, Column 7, line 13, should read -- 151 --

Column 9, line 14, the word reading "or" should read -- of --.

Signed and Sealed this

Twenty-fourth Day of January 1978

[SEAL]

Attest:

RUTH C. MASON
*Attesting Officer*

LUTRELLE F. PARKER
*Acting Commissioner of Patents and Trademarks*